United States Patent
Shin et al.

(10) Patent No.: US 11,753,636 B2
(45) Date of Patent: *Sep. 12, 2023

(54) METHOD FOR ENRICHING PATHOGEN, USING HOMOBIFUNCTIONAL IMIDOESTER

(71) Applicant: INFUSION TECH, Anyang-si (KR)

(72) Inventors: Yong Shin, Seoul (KR); Choong Eun Jin, Suwon-si (KR)

(73) Assignee: INFUSION TECH, Anyang-si (KR)

( * ) Notice: Subject to any disclaimer, the term of this patent is extended or adjusted under 35 U.S.C. 154(b) by 502 days.

This patent is subject to a terminal disclaimer.

(21) Appl. No.: 16/756,851

(22) PCT Filed: Oct. 18, 2018

(86) PCT No.: PCT/KR2018/012337
§ 371 (c)(1),
(2) Date: Apr. 17, 2020

(87) PCT Pub. No.: WO2019/078638
PCT Pub. Date: Apr. 25, 2019

(65) Prior Publication Data
US 2021/0189378 A1    Jun. 24, 2021

(30) Foreign Application Priority Data

Oct. 18, 2017   (KR) ................. 10-2017-0135265
Oct. 18, 2018   (KR) ................. 10-2018-0124183

(51) Int. Cl.
*C12N 15/10*   (2006.01)
*G01N 1/40*    (2006.01)

(52) U.S. Cl.
CPC ....... *C12N 15/1006* (2013.01); *G01N 1/4044* (2013.01)

(58) Field of Classification Search
CPC ..... C12N 15/1006; C12Q 1/6806; C12Q 1/24
See application file for complete search history.

(56) References Cited

U.S. PATENT DOCUMENTS

2002/0012922 A1* 1/2002 Hilbush ............. C12N 15/1096
                                                    435/6.16
2015/0322486 A1  11/2015 Shin et al.

FOREIGN PATENT DOCUMENTS

| | | |
|---|---|---|
| EP | 2776575 B1 | 3/2017 |
| EP | 3460072 A1 | 3/2019 |
| EP | 3505628 A1 | 7/2019 |
| JP | 2010006788 A | 1/2010 |
| KR | 10-2015-0096444 A | 8/2015 |
| KR | 10-2017-0064540 A | 6/2017 |
| KR | 10-2017-0129591 A | 11/2017 |
| WO | 01/38637 A1 | 5/2001 |
| WO | 2004/045647 A1 | 6/2004 |
| WO | 2008/124483 A1 | 10/2008 |
| WO | 2010078399 A2 | 7/2010 |
| WO | 2017/127684 A1 | 7/2017 |

OTHER PUBLICATIONS

Han et al., Lab Chip, 2016, 16, p. 132-141, First Published Oct. 27, 2015. (Year: 2015).*
Yang et al., Journal of Microelectromechanical Systems, 2011, 20(4), p. 819-827. (Year: 2011).*
Yadav et al., Materials Science and Engineering C, 2014, 35, p. 283-290. (Year: 2014).*
Jin et al., Analytical Chemistry, 2017, 89, p. 7502-7510 and supporting information, published Jun. 21, 2017. (Year: 2017).*
Huang et al., Environ. Sci. Technol., 2010, 44, p. 7908-7913. (Year: 2010).*
International Search Report for PCT/KR2018/012337 dated May 8, 2019 from Korean Intellectual Property Office.
Shin, Y. et al., "Dimethyl adipimidate/Thin film Sample processing (DTS); A simple, low-cost, and versatile nucleic acid extraction assay for downstream analysis", Scientific Reports, 2015, vol. 5, Article number; 14127, pp. 1-11.
Shin, Y. et al., "Solid phase nucleic acid extraction technique in a microfluidic chip using a novel non-chaotropic agent: dimethyl adipimidate", Lab on a Chip, 2014, vol. 14, No. 2, pp. 359-368.
Suter, J.D. et al., "Label-free DNA methylation analysis using opto-fluidic ring resonators", Biosensors and Bioelectronics. 2010. vol. 26, No. 3, pp. 1016-1020.
Graciela Glikmann et al, "Soluble immune complexes in cerebrospinal fluid of patients with multiple sclerosis and other neurological diseases", Acta neuro, scandinav, vol. 61, Jun. 1980, pp. 333-343.
Choong Eun Jin et al, "Use of Dimethyl Pimelimidate with Microfluidic System for Nucleic Acids Extraction without Electricity", Analytical Cheminstry, vol. 89, No. 14, Jul. 5, 2017, pp. 7502-7510.
Qing Liu et al., "Two-stage sample-to-answer system based on nucleic acid amplification approach for detection of malaria parasites", Biosensor and Bioelectronics, vol. 82, Mar. 22, 2016, pp. 1-8.
Lu Zhang et al., "Point-of-care-testing of nucleic acids by microfluidics", TrAC Trends in Analytical Chemistry, vol. 94, Sep. 2017, pp. 106-116.

(Continued)

*Primary Examiner* — Jonathan S Lau
(74) *Attorney, Agent, or Firm* — Revolution IP, PLLC

(57) ABSTRACT

The present invention relates to a method of enriching a pathogen using an homobifunctional imidoester group, and the method of enriching a pathogen and extracting nucleic acids using homobifunctional imidoester compound (DMA, DMP, DMS) according to the present invention can quickly extract a small amount of pathogen contained in a sample without the use of special equipment and can be used as in situ diagnosis, and since it is possible to enrich a pathogen and extract nucleic acids simultaneously in one tube or a chip, it has the advantage of being more efficient than the conventional method, saving time and cost, and being easy to use.

14 Claims, 3 Drawing Sheets

Specification includes a Sequence Listing.

(56) References Cited

OTHER PUBLICATIONS

Choong Eun Jin et al., "Simple and label-free pathogen enrichment via homobifunctional imidoesters using a microfluidic (SLIM) system for ultrasensitive pathogen detection in various clinical specimens", Biosensors and Bioelectronics, vol. 111, Jul. 15, 2018, pp. 66-73.

\* cited by examiner

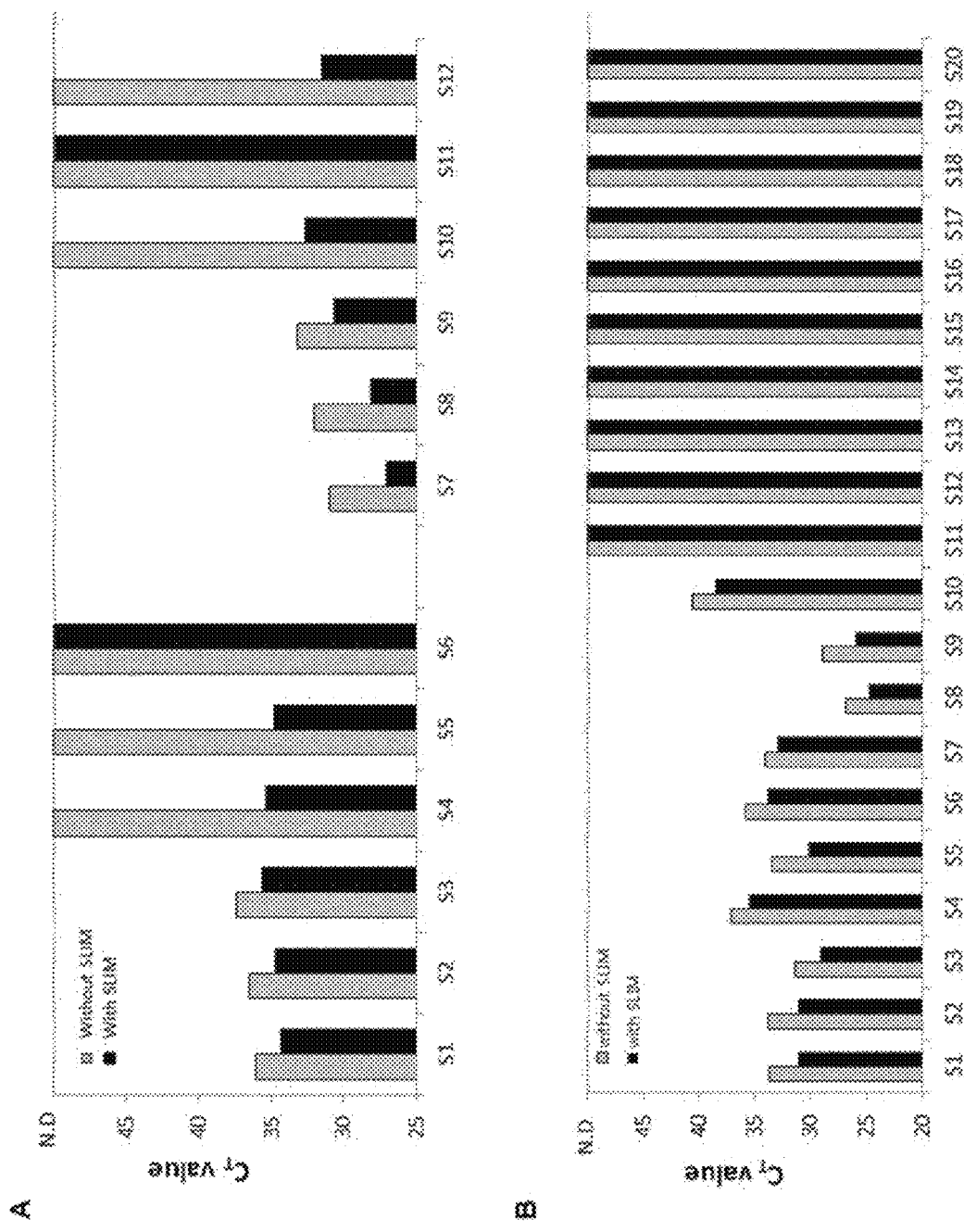
[FIG. 3]

METHOD FOR ENRICHING PATHOGEN, USING HOMOBIFUNCTIONAL IMIDOESTER

TECHNICAL FIELD

The present invention relates to a method of enriching a pathogen using a homobifunctional imidoester (HI) compound, more specifically, to a method of enriching a pathogen using dimethyl adipimidate (DMA), dimethyl pimelimidate (DMP) or dimethyl suberimidate (DMS).

BACKGROUND ART

Nucleic acids are an important analytical tool for identifying disease states, and DNA biomarkers such as single nucleotide polymorphism (SNP), mutations or DNA methylation can help researchers find the cause of cancer, diagnose and observe the condition of the disease during the early stages of the disease, which provides important clues to give great opportunities for prognosis and surveillance.

Nucleic acids such as DNA are present at very low physiological concentrations compared to other components such as proteins (e.g. tens of nanograms of DNA per microliter of whole blood versus tens of micrograms of protein), effectively extracting DNA from clinical samples and pre-concentration is very important for subsequent processes such as amplification and detection. In the case of methylated DNA, this problem is even more important.

Conventional methods for microbial detection could not use the entire solution from patient samples, and have extracted nucleic acids using only a portion of them for the detection. In the case of a large amount of microorganisms, there is no big problem, but in the case of a small amount of microorganisms, it is not possible to accurately detect them and to cause problems in controlling additional infectious diseases and thus studies on the concentration method for using all microorganisms in the sample as much as possible are needed.

In addition, recently, as more and more purified nucleic acids are used in various fields such as diagnostic medicine, pharmacy medicine, metabolic medicine including biotechnology, efforts to isolate nucleic acids from various biological samples more rapidly and purely have continued.

However, the biggest advancement in the method of isolating nucleic acids up to now has been directed to carriers that specifically adsorb only nucleic acids from various types of substances contained in cell lysis solutions, such as genomic DNA, plasmid DNA, messenger RNA, proteins, and cell debris particles. The focus of almost all research, including this technology, has been limited to research and development of substances adsorbing nucleic acids.

Accordingly, in order to separate nucleic acids more rapidly and purely, it is urgent to develop a technology capable of quickly separating only desired nucleic acids from cell debris particles, protein-denatured aggregates and various other cell decomposition substances.

DISCLOSURE

Technical Problem

The object of the present invention is to provide a composition for enriching a pathogen comprising an homobifunctional imidoester compound, a method and a kit for enriching a pathogen using the same; a composition for enriching a pathogen and extracting nucleic acids comprising an homobifunctional imidoester compound, a method of enriching a pathogen and extracting nucleic acids using the same, and a kit thereof.

Technical Solution

In order to achieve the above object, the present invention provides a composition for enriching a pathogen comprising a compound represented by the following Chemical Formula 1:

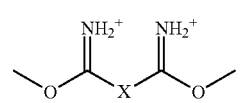

[Chemical Formula 1]

wherein X is $(CH_2)_n$ and n is an integer from 4 to 10.

Also, the present invention provides a kit for enriching a pathogen comprising the composition.

In addition, the present invention provides a method of enriching a pathogen comprising: a first step of modifying by introducing an amine group to an object; and a second step of contacting a sample containing a pathogen on a modified object with a compound represented by the following Chemical Formula 1,

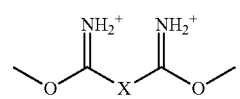

[Chemical Formula 1]

wherein X is $(CH_2)_n$ and n is an integer from 4 to 10.

In addition, the present invention provides a composition for enriching a pathogen and extracting nucleic acids comprising a compound represented by the following Chemical Formula 1:

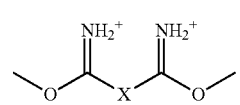

[Chemical Formula 1]

wherein X is $(CH_2)_n$ and n is an integer from 4 to 10.

Furthermore, the present invention provides a kit for enriching a pathogen and extracting nucleic acids comprising the composition.

In addition, the present invention provides a method of enriching a pathogen and extracting nucleic acids from an enriched pathogen simultaneously, comprising: a first step of modifying by introducing an amine group to an object; a second step of contacting a sample containing a pathogen on a modified object with a compound represented by the following Chemical Formula 1; a third step of separating nucleic acids from an enriched pathogen; a fourth step of forming a complex of separated nucleic acids and the compound; and a fifth step of extracting the nucleic acids by treating an elution buffer with the object in which the complex is formed,

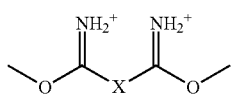

wherein X is $(CH_2)_n$ and n is an integer from 4 to 10.

Advantageous Effects

A method of enriching a pathogen and extracting nucleic acids using homobifunctional imidoester compound (DMA, DMP, DMS) according to the present invention can quickly extract a small amount of pathogen contained in a sample without the use of special equipment and can be used as in situ diagnosis, and since it is possible to enrich a pathogen and extract nucleic acids simultaneously in one tube or a chip, it has the advantage of being more efficient than the conventional method, saving time and cost, and being easy to use.

DESCRIPTION OF DRAWINGS

FIG. 3 shows the results of pathogen enrichment and nucleic acids extraction from a sample of patients with parainfluenza infection (A); and pathogen enrichment and nucleic acids extraction from a sample of patients with herpes zoster (B) using the homobifunctional imidoester compound.

BEST MODE

Figure 1:
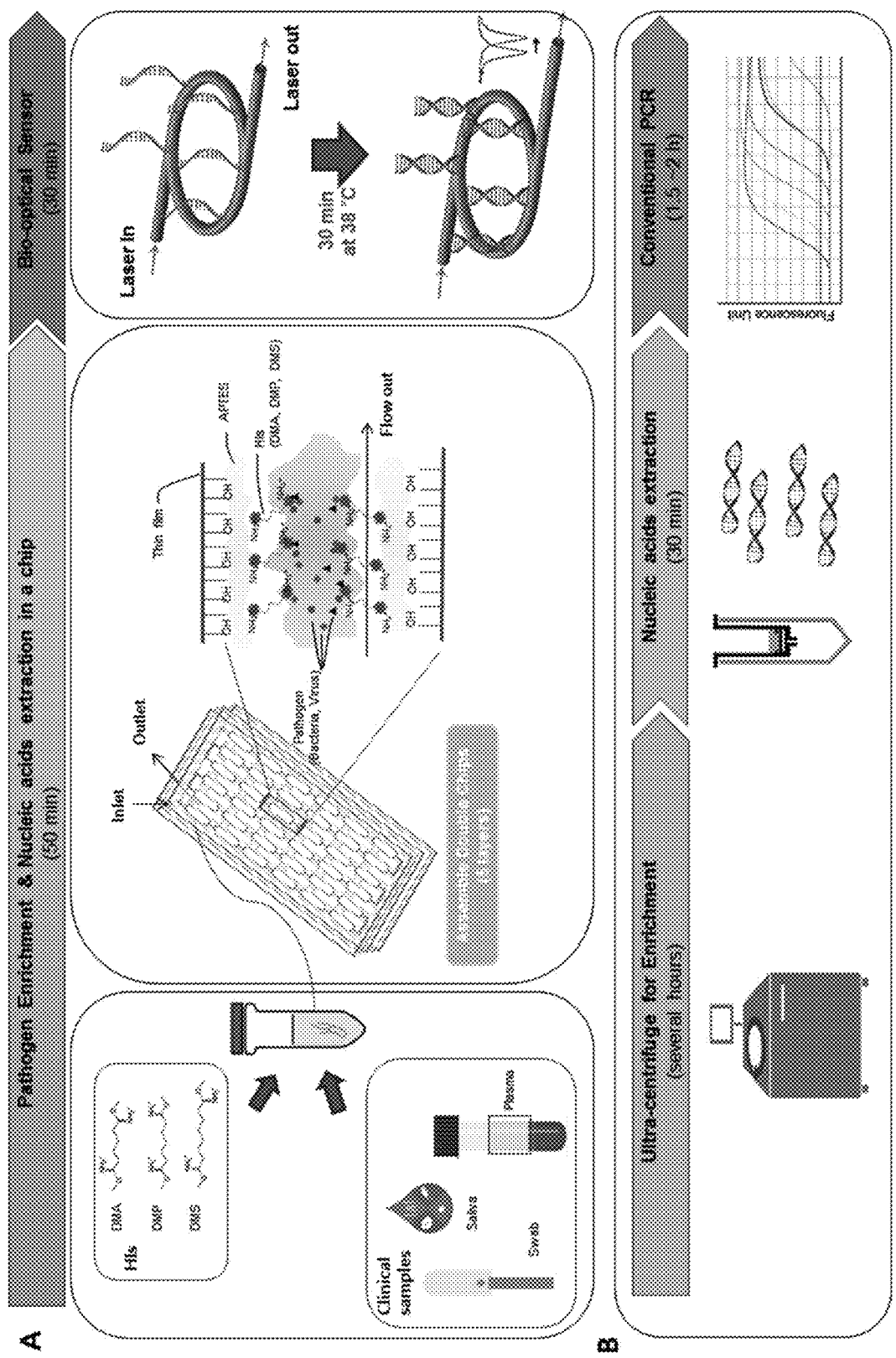
FIG. 1 shows a schematic diagram of a thin film device for enriching a pathogen and extracting nucleic acids using a homobifunctional imidoester compound, and a pathogen enrichment and nucleic acids sample analysis according to the present invention.

Hereinafter, the present invention will be described in more detail.

The inventors of the present invention have developed a method of enriching a small amount of pathogen contained in a sample and extracting nucleic acids from the enriched pathogen, and found out that the method of enriching the pathogen and extracting nucleic acids according to the present invention is more convenient and less expensive than the conventional method and it is possible to enrich the pathogen and extract nucleic acids at the same time and to diagnose immediately on site without using large equipment, and completed the present invention.

The present invention provides a composition for enriching a pathogen comprising a compound represented by the following Chemical Formula 1:

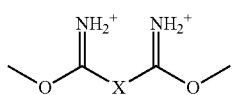

[Chemical Formula 1]

wherein X is $(CH_2)_n$ and n is an integer from 4 to 10.

The pathogen may be microorganism, and the microorganism may be a virus, bacteria, fungi, protozoa, *Rickettsia* or *spirochaeta*, but it is not limited thereto.

Also, the present invention provides a kit for enriching a pathogen comprising the composition.

In addition, the present invention provides a method of enriching a pathogen comprising: a first step of modifying by introducing an amine group to an object; and a second step of contacting a sample containing a pathogen on a modified object with a compound represented by the following Chemical Formula 1,

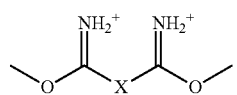

[Chemical Formula 1]

wherein X is $(CH_2)_n$ and n is an integer from 4 to 10.

The object of the first step may be a solid material or a solid support, for example, it may be any one of a thin film device, a magnetic bead, a ring resonator or a nanoparticle, but it is not limited thereto.

The object of the first step may be modified with a silane compound. Preferably, the silane compound may be a compound represented by the following Chemical Formula 2, but it is not limited thereto:

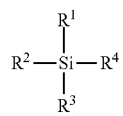

[Chemical Formula 2]

wherein each of $R^1$ to $R^3$ may be same or different, and are any one of C1 to C4 alkyl or C1 to C4 alkoxy, and $R^4$ is any one of amino (C1 to C10) alkyl, 3-(2-amino (C1 to C4)alkylamino) (C1 to C4)alkyl or 3-[2-(2-amino (C1 to C4)alkylamino) (C1 to C4) alkylamino] (C1 to C4)alkyl.

More preferably, the silane compound may be at least one selected from the group consisting of (3-aminopropyl) triethoxysilane (APTES), (3-aminopropyl)trimethoxysilane), (1-aminomethyl)triethoxysilane, (2-aminoethyl)triethoxysilane, (4-aminobutyl)triethoxysilane), (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl]diethylenetriamine, [3-(2-aminoethylamino)propyl]trimethoxysilane (AEAPTMS) and 3-[(trimethoxysilyl)propyl]diethylenetriamine (TMPTA), but it is not limited thereto.

The sample containing a pathogen may be any one selected from the group consisting of feces, urine, tears, saliva, external secretions from skin, external secretions from respiratory tract, external secretions from intestinal tract, external secretions from digestive tract, plasma, serum, blood, spinal fluid, lymph fluid, body fluids and tissues of object suspected of being infected with the pathogen, but it is not limited thereto.

In addition, the present invention provides a composition for enriching a pathogen and extracting nucleic acids comprising a compound represented by the following Chemical Formula 1:

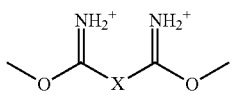

[Chemical Formula 1]

wherein X is $(CH_2)_n$ and n is an integer from 4 to 10.

The pathogen may be microorganism, and the microorganism may be a virus, bacteria, fungi, protozoa, *Rickettsia* or *spirochaeta*, but it is not limited thereto.

The nucleic acids may be DNA or RNA.

In addition, the present invention provides a kit for enriching a pathogen and extracting nucleic acids comprising the composition. The kit may additionally comprise a buffer and the like required for the effective nucleic acids extraction.

Furthermore, the present invention provides a method of enriching a pathogen and extracting nucleic acids from an enriched pathogen simultaneously, comprising: a first step of modifying by introducing an amine group to an object; a second step of contacting a sample containing a pathogen on a modified object with a compound represented by the following Chemical Formula 1; a third step of separating nucleic acids from an enriched pathogen; a fourth step of forming a complex of a separated nucleic acids and the compound; and a fifth step of extracting the nucleic acids by treating an elution buffer with the object in which the complex is formed,

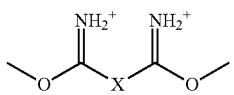

[Chemical Formula 1]

wherein X is $(CH_2)_n$ and n is an integer from 4 to 10.

The pathogen may be microorganism, and the microorganism may be a virus, bacteria, fungi, protozoa, *Rickettsia* or *spirochaeta*, but it is not limited thereto.

The object of the first step may be a solid material or a solid support, for example, it may be any one of a thin film device, a magnetic bead, a ring resonator or a nanoparticle, but it is not limited thereto.

The object of the first step may be modified with a silane compound. Preferably, the silane compound may be a compound represented by the following Chemical Formula 2, but it is not limited thereto:

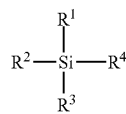

[Chemical Formula 2]

wherein each of $R^1$ to $R^3$ may be same or different, and are any one of C1 to C4 alkyl or C1 to C4 alkoxy, and $R^4$ is any one of amino (C1 to C10) alkyl, 3-(2-amino (C1 to C4)alkylamino) (C1 to C4)alkyl or 3-[2-(2-amino (C1 to C4)alkylamino) (C1 to C4) alkylamino] (C1 to C4)alkyl.

More preferably, the silane compound may be at least one selected from the group consisting of (3-aminopropyl) triethoxysilane (APTES), (3-aminopropyl)trimethoxysilane), (1-aminomethyl)triethoxysilane, (2-aminoethyl)triethoxysilane, (4-aminobutyl)triethoxysilane), (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl]diethylenetriamine, [3-(2-aminoethylamino)propyl]trimethoxysilane (AEAPTMS) and 3-[(trimethoxysilyl)propyl]diethylenetriamine (TMPTA), but it is not limited thereto.

The sample containing a pathogen may be any one selected from the group consisting of feces, urine, tears, saliva, external secretions from skin, external secretions from respiratory tract, external secretions from intestinal tract, external secretions from digestive tract, plasma, serum, blood, spinal fluid, lymph fluid, body fluids and tissues of object suspected of being infected with the pathogen, but it is not limited thereto.

Hereinafter, examples of the present invention will be described in detail to understand the present invention. The present invention may, however, be embodied in many different forms and should not be limited to the embodiments set forth herein in order to clearly illustrate the present invention for those skilled in the art to which the present invention pertains.

FIG. 1 shows a method of enriching a pathogen and extracting nucleic acids using a homobifunctional imidoester (HI; DMA, DMP, DMS) compound in the thin film device of the present invention which includes three steps of sample culture, washing and elution. The surface of the thin film device is modified with an amine using an amine-based solution, and the hydrophobicity of the film device is modified to the hydrophilicity.

When nucleic acids sample, elution buffer, and HI solution (DMA, DMP, DMS) are injected on the modified thin film device, a crosslinking mechanism between nucleic acids and HI is caused by the interaction between the amino group of the nucleic acids and the bifunctional amine group of HI and a complex between nucleic acids and the HI is formed to extract DNA from the sample.

EXAMPLE 1

Fabrication and Pretreatment of Homobifunctional Imidoester (HI) Based Thin Film Device (1) Fabrication of Thin Film Devices A low cost thin film device for use as a microfluidic device (closed device) was fabricated by using a $CO_2$ laser cutting machine (VLS3.50 (610×305 mm); Universal Laser Systems, Scottsdale, Ariz.). The thin film device is composed of an upper thin film and a lower thin film, and a microfluidic chamber interposed between the upper thin film and the lower thin film. The thin film device consists of a microfluidic chamber of a single microchannel combined with a homobifunctional imidoester (HI) for pathogen enrichment.

In contrast to the Qiagen kit (open device), the microfluidic chamber of the device is based on a closed device to prevent contamination caused by the open device. During the cleaning and elution steps, the reaction sample remains in the microfluidic chamber of the sealed device to reduce contamination. Repeated rapid expansion and contraction in the flow cross-sectional area can generate microvortices by liquid sample injection.

To enrich the pathogen from the sample, the 36 slots-type micro wells of the chamber were connected at an expansion and contraction ratio of 1:5.6 and 5.6:1, respectively. The microfluidic chip was designed using AutoCAD (Autodesk, Inc., San Rafael, Calif.) and printed with a laser cutting machine used to manufacture a prototyping device having the advantages of low cost, simplicity and speed.

To produce a 3D disposable chip consisting of three layers composed of a 300 μm thick double sided tape (Adhesive 300LSE-9495LE, 3M, USA)) as an inner layer and two 100 μm thick thin films (Kemafoil hydrophilic film, HNW-100, COVEME, Italy) as outer layers using a laser cutter (10.6μ $CO_2$ laser source with an electric power range of 10 W to 50 W). The outer layer was attached to the permanent adhesive surfaces of the top and bottom of the inner layer to create a 3D disposable chip for the HI reaction. The height of the microfluidic chamber is about 300 μm and the total volume thereof is set to 300 μl.

To control the sample flow in the micro-channel, a tubing adapter was prepared by attaching cast acrylic sheet (Marca CIPTA, Indonesia) having a thickness of 3 mm to one side of a double-sided tape, and cutting and punching with a laser cutting machine. The fabricated adapter was attached to the inlet and outlet of the 3D disposable chip, respectively. Thereafter, pre-cut Tygon® tubing (AAC02548; Cole-Farmer, Vernon Hills, Ill.) was placed in the adapter hole and sealed using a thermally stable epoxy at 120° C.

2) Thin Film Device Pretreatment

To facilitate the use of a thin film device for nucleic acids extraction, a plastic cartridge was manufactured using a laser cutter. Plastic cartridges (top and bottom) serve to hold the 3D disposable chip during analysis; 105 mm long, 60 mm wide, 10 mm high. The layout of each plastic component was designed using AutoCAD. The structure was patterned on a sheet of acrylonitrile butadiene styrene (ABS) using a milling machine. After mounting the chip on the lower plastic part, the device was constructed by assembling with the upper plastic part using four wrench bolts.

Finally, in order to use a thin film device for pathogen enrichment and HI as a non-chaotropic reagent, a surface modification protocol was performed. Briefly, in order to generate an amine group on the inner surface of the 3D disposable chip, the inner surface was firstly treated with oxygen plasma (Covance Model, Femtoscience) for 10 minutes to change the properties of the inner surface from hydrophobic to hydrophilic and the plasma-treated thin film device was immersed in a 2% 3-aminopropyl triethoxysilane (APTES, Sigma-Aldrich) aqueous solution at 65° C. for 60 minutes, and then thoroughly washed with deionized water. After washing, in order to cure the thin film device, the washed thin film device was quickly dried under a stream of nitrogen to modify the thin film device with an amine.

Through the measurement of the water contact angle of the amine-modified thin film device using a Drop Shape Analyzer (DSA100, KRUSS, Germany), it was found that the hydrophilicity of the thin film device was changed significantly with temperature and incubation time. After silanization of the thin film device with APTES for 60 minutes at 65° C., the hydrophilicity of the thin film surface increased (about 30 to 40° C.). The device can be stored at room temperature until use.

EXAMPLE 2

HI/Thin Film Sample Analysis

Analysis conditions and reactions for enriching pathogens were optimized using the thin film device of the present invention (simple and label-free pathogen enrichment via homobifunctional imidoesters using a microfluidic; SLIM). Since HI can capture nucleic acids through complex formation on the surface of thin films, to compare pathogen binding capacity, experiments were performed using various HI such as dimethyl adipimidate (DMA), dimethyl pimelimidate (DMP) and dimethyl suberimidate (DMS). All HI reagents were purchased from Sigma-Aldrich (St. Louis, Mo.).

To perform the reaction, 2 ml of a sample of patients with severe fever with thrombocytopenia syndrome (SFTS) was obtained by swab method and was mixed with 1 ml of *E. coli* culture sample and 300 μl of HI solution at a concentration of 100 mg/ml, respectively and then injected into the device at a rate of 100 μl/min using a pump syringe (KD Scientific, Mass.) and the device was left at room temperature for 10 minutes to capture pathogens from the sample. Pathogens enriched by HI (DMA, DMP, DMS) were collected in a few minutes using elution buffer (10 mM sodium bicarbonate, pH<10.6, flow rate: 50 μl/min).

In order to compare the enrichment ability in the above experiment, nucleic acids were extracted by QIAamp® DNA mini kit or QIAamp® viral RNA mini kit (Qiagen, Germany), and experiments were performed according to the protocol provided by the manufacturer.

In addition, to perform pathogen enrichment and nucleic acids extraction using the thin film device of the present invention, nucleic acids were extracted by referring to the previously reported paper (Scientific reports, 5, 14127., Analytical Chemistry, 89 (14), 7502-7510).

The eluted nucleic acids sample contains 10 μl of proteinase K, 10 μl of DNase (RNA only), 100 μl of self-lysis buffer (100 mM Tris-HCl (pH 8.0), 10 mM ethylenediaminetetraacetic acid, 1% lauryl sodium sulfate, and 10% Triton X-100) and 100 μl of HI (100 mg/ml) were mixed. After incubating the device at 56° C. (for DNA) or room temperature (for RNA) for 20 minutes, the device was washed with PBS to remove debris from the sample. Nucleic acids were extracted in minutes using elution buffer (pH>10.6). The amount and purity of the extracted nucleic acids were analyzed by measuring the ratio of the optical density of the sample at 260 nm and 280 nm using Nano Drop (Thermo Fisher Scientific, USA).

EXAMPLE 3

Pathogen (*E. coli*) Enrichment and Nucleic Acids Extraction using HI

To confirm the enrichment of the pathogen using a thin film device, the basic characteristics of the device were analyzed in a culture sample of *Escherichia coli* (ATCC 25922). The colony formation unit (CFU) of *E. coli* was calculated using a standard agar medium (plate count agar, PON BD difco), and optimal HI reagent (DMA, DMP, DMS) was evaluated using 1 ml of *E. coli* sample ($10^4$ CFU $ml^{-1}$).

The rodA gene was amplified from the extracted DNA using a Qiagen kit and a thin film device. PCR conditions include an initial denaturation step for 15 minutes at 95° C., 30 seconds at 95° C., 30 seconds at 60° C., 30 seconds at 72° C., 40 cycles; a final elongation step for 7 minutes at 72° C. 5 μl of DNA was amplified to a total volume of 25 μl containing 10×PCR buffer (Qiagen), 5 mM $MgCl_2$, 0.25 mM deoxynucleotide triphosphate, 25 pmol of each primer and 1 unit Taq DNA polymerase (Qiagen).

Real-time PCR was performed with reference to the AriaMx real-time PCR instrument protocol (Agilent technologies). PCR conditions were 15 minutes at 95° C., 10 seconds at 95° C., 20 seconds at 60° C., 20 seconds at 72° C., 40 cycles; cooling step of 30 seconds at 40° C. 5 μl of DNA was amplified to a total volume of 20 µl containing 10 µl 2× Brillient III SYBR Green qPCR maste mix, 25 pmol of each primer and DI water. The SYBR Green signal of the amplified product was obtained using AriaMx real-time PCR (Agilent technologies), and detailed sequences of the primer sets are shown in Table 1 below.

TABLE 1

| Targets | Sequence (5' → 3') | Product size (bp) |
|---|---|---|
| rodA (E. Coli) | F: GCA AAC CAC CTT TGG TCG<br>R: CTG TGG GTG TGG ATT GAC AT | 195 |
| S segment (SFTS) | F: CAG CCA CTT TAC CCG AAC AT<br>R: GGC CTA CTC TCT GTG GCA AG | 150 |

Figure 2:
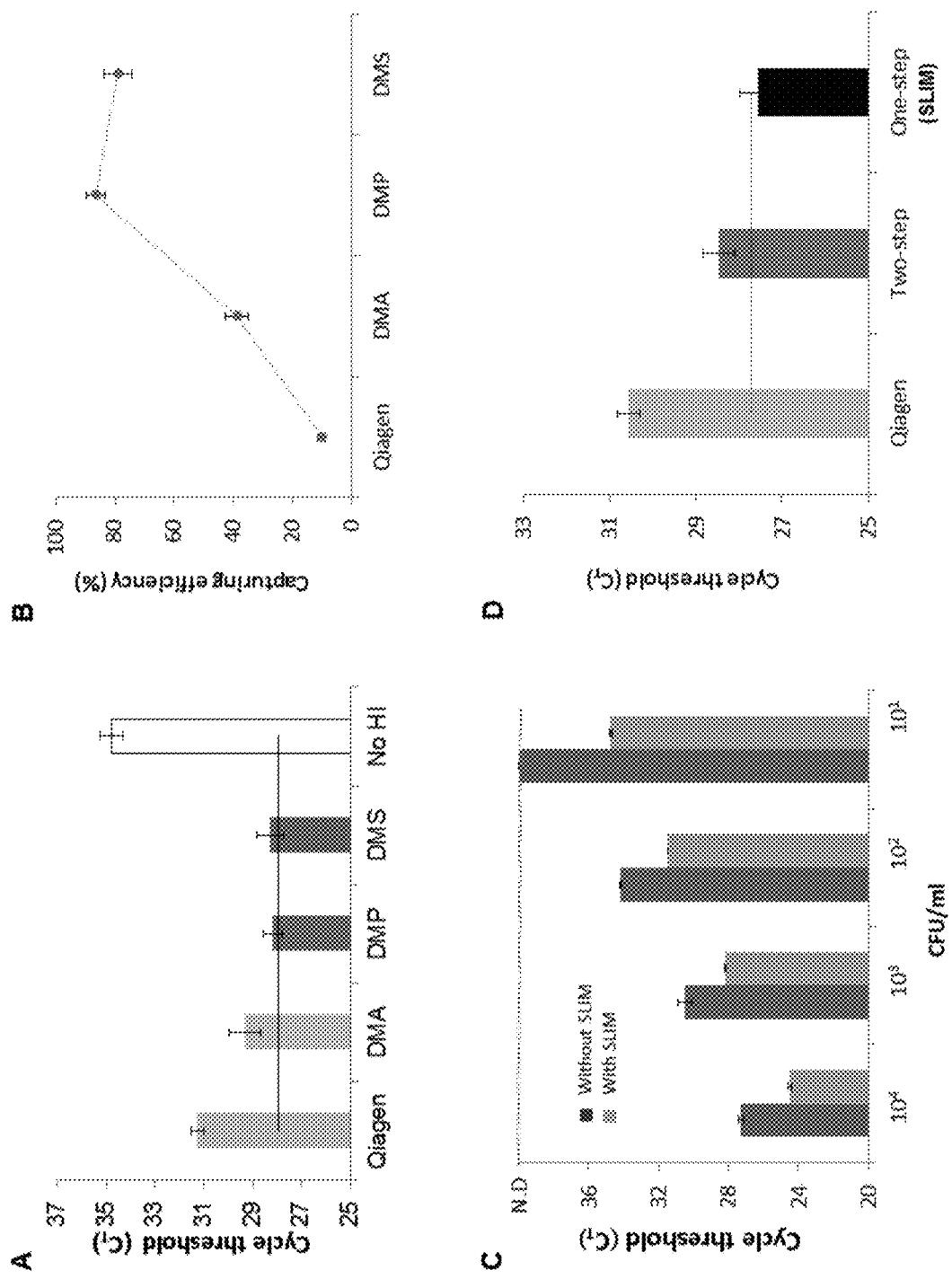
FIG. 2 shows pathogen (*E. coli*) enrichment and nucleic acids extraction (A); pathogen capture efficiency (B); pathogen enrichment and nucleic acids extraction according to pathogen concentration (C); and the results of one-step pathogen enrichment and nucleic acids extraction (D) using homobifunctional imidoester compound.

Referring to FIG. 2A and FIG. 2B, in order to enrich the pathogen, 1 ml of E. coli sample was mixed with 300 µl of HI solution (100 mg·ml$^{-1}$), and then injected into the device, and concentrated at a flow rate of 100 µl/min at room temperature. The enriched sample was extracted with DNA using the Qiagen DNA kit, and real-time PCR was performed to compare pathogen enrichment efficiency. As a result, it was confirmed that when the pathogen is enriched using HI (DMA, DMS, DMP), the detection sensitivity is improved by reducing the Ct value than when the nucleic acids are extracted without the enrichment step using the conventional Qiagen kit method, and the pathogen enrichment efficiency of DMP among HI was the best. HI reagent concentration (100 mg·ml$^{-1}$), HI reagent type (DMP), and incubation time (20 min) were optimized for the pathogen enrichment.

After optimizing the conditions for the pathogen enrichment, the efficiency of pathogen enrichment and nucleic acids extraction by the thin film apparatus (SLIM) of the present invention was analyzed using 1 ml of an E. coli sample ($10^1$-$10^4$ CFU ml$^{-1}$). As a result, referring to FIG. 2C, it was confirmed that the DNA was amplified from the concentrated E. coli and the Ct value increased with continuous dilution. E. coli samples at all concentrations in the thin film device of the present invention showed a reduced Ct value than those of the conventional Qiagen kit, indicating that the DNA enrichment efficiency is excellent. It was confirmed that the detection limit was also 10 times superior to the conventional Qiagen kit.

Next, it was analyzed whether the thin film device of the present invention is capable of pathogen enrichment and nucleic acids extraction simultaneously on the same platform. The one-step process (pathogen enrichment and nucleic acids extraction from one chip) and two-step process (pathogen enrichment and nucleic acids extraction from two separate chips, respectively) were compared to the conventional Qiagen kits. As a result, referring to FIG. 2D, it was confirmed that the detection sensitivity is improved by reducing the Ct value in the one-step process, and that pathogen enrichment and extraction can be performed simultaneously in one chip (or tube).

EXAMPLE 4

Pathogen (Virus) Enrichment and Nucleic Acids Extraction using SFTS Patient Samples A total of 5 swab samples were provided from SFTS patients, and nasopharyngeal swab/inhaler was used as part of the clinical trial. Dacron swabs, pre-applied with viral carrier media, were used to aseptically clean surfaces frequently touched by patients or health care workers. When using the QIAamp Viral RNA mini kit in 2 ml of the sample collected by the swab method, 140 µl was used, and when using the thin film device, viral RNA was extracted using 2 ml of the entire sample. Samples were eluted using 60 µl of elution buffer, and the eluted DNA was stored at −20° C. until use.

Next, the S portion of the SFTS virus was amplified from the eluted RNA using the Qiagen kit and the thin film device. One-step reverse transcript (RT) PCR consists of an initial denaturation at 50° C. for 30 minutes; 30 cycles at 95° C., 30 seconds at 60° C., 30 seconds at 72° C., 50 cycles; a final elongation at 72° C. for 10 minutes.

5 µl of RNA was amplified to a total volume of 25 µl containing 5× OneStep RT-PCR buffer (Qiagen), 0.25 mM deoxynucleotide triphosphate, 25 pmol of each primer and 1 unit of OneStep RT-PCR Enzyme mix (Qiagen). Quantitative RT-PCR was performed with reference to the AriaMx real-time PCR instrument protocol (Agilent technologies).

5 µl of RNA was amplified to 20 µl of a total volume of containing 10 µl of 2× Brillient III SYBR Green qPCR maste mix, 25 pmol of each primer and DI water. PCR conditions consist of 30 min at 50° C. and 10 min at 95° C., 10 seconds at 95° C., 20 seconds at 60° C., 20 seconds at 72° C., 50 cycles; cooling step of 30 seconds at 40° C. The SYBR Green signal of the amplified product was obtained using AriaMx real-time PCR (Agilent technologies), and detailed sequences of the primer sets are shown in Table 1 above.

TABLE 2

| No. | Sample | | $C_t$ |
|---|---|---|---|
| 1 | SETS patients | Sample 1 | Qiagen (140 µl) |
| 2 | | | DMP enrich (2 ml) 39.81- |
| 3 | | Sample 2 | Qiagen (140 µl) — |
| 4 | | | DMP enrich (2 ml) — |
| 5 | | Sample 3 | Qiagen (140 µl) 43.26 |
| 6 | | | DMP enrich (2 ml) 39.24 |
| 7 | | Sample 4 | Qiagen (140 µl) — |
| 8 | | | DMP enrich (2 ml) 40.9 |
| 9 | | Sample 5 | Qiagen (140 µl) — |
| 10 | | | DMP enrich (2 ml) 39.14 |

Referring to Table 2, while the conventional Qiagen method could not detect viruses in samples of SFTS patients (Samples 1, 4, 5), when using the thin film device of the present invention, concentration of viruses and nucleic acids extraction contained in the samples are possible at the same time and it was confirmed that it can be utilized for virus detection.

EXAMPLE 5

Pathogen (Virus) Enrichment and Nucleic Acids Extraction using Parainfluenza (hPIV-3) and Herpes Zoster (HZ) Patient Samples Swab samples were provided from surfaces in contact with the patient during parainfluenza (hPIV-3) outbreaks between May and June 2016. When using the QIAamp Viral RNA mini kit in 2 ml of the sample collected by the swab method, 140 µl was used and when using the thin film device, viral RNA was extracted by using 2 ml of the entire sample. Samples were eluted using 60 µl of elution buffer and the eluted DNA was stored at −20° C. until use.

Next, the S portion of the SFTS virus was amplified from the eluted RNA using the Qiagen kit and the thin film device. One-step reverse transcript (RT) PCR consists of an initial denaturation at 50° C. for 30 minutes; 30 cycles at 95° C., 30 seconds at 60° C., 30 seconds at 72° C., 50 cycles; a final elongation at 72° C. for 10 minutes.

5 μl of RNA was amplified to a total volume of 25 μl containing 5× OneStep RT-PCR buffer (Qiagen), 0.25 mM deoxynucleotide triphosphate, 25 pmol of each primer and 1 unit of OneStep RT-PCR Enzyme mix (Qiagen). Quantitative RT-PCR was performed with reference to the AriaMx real-time PCR instrument protocol (Agilent technologies).

5 μl of RNA was amplified to 20 μl of a total volume of containing 10 μl of 2× Brillient III SYBR Green qPCR maste mix, 25 pmol of each primer and DI water. PCR conditions consist of 30 min at 50° C. and 10 min at 95° C., 10 seconds at 95° C., 20 seconds at 60° C., 20 seconds at 72° C., 50 cycles; cooling step of 30 seconds at 40° C. The SYBR Green signal of the amplified product was obtained using AriaMx real-time PCR (Agilent technologies) and detailed sequences of the primer sets are shown in Table 1 above.

As a result, referring to FIG. 3A, while the virus could not be detected in the samples (S4, S5, S10, S12) of some hPIV-3 patients by the conventional Qiagen method, it was confirmed that in the case of using the thin film device of the present invention, enrichment virus contained in the sample and nucleic acids extraction were possible simultaneously, and thus it could be used for virus detection.

Next, the thin film device of the present invention was applied to a saliva sample of a herpes zoster (HZ) patient. Chicken pox and HZ are known to be caused by the varicella-zoster virus (VZV), and the rash of HZ is generally considered sufficient for clinical diagnosis, but saliva and plasma samples need to be analyzed in order to distinguish between HZ such as the herpes simplex virus and HZ mimic diseases. On the other hand, in the detection of VZV, saliva DNA (88%) has been reported to have a much higher PCR analysis sensitivity than plasma DNA (28%), but there is disadvantage that collecting saliva samples from plasma samples from HZ patients is painful.

Thus, in the present invention, a thin film device was applied to analyze the enrichment efficiency of two samples using saliva and plasma samples. First, 1 ml of saliva sample was used to extract VZV enrichment and viral DNA, and 10 saliva positive samples were selected by performing real-time PCR. All positive samples identified using the ORF62 region of VZV showed initial Ct values. On the other hand, it was confirmed that none of the negative samples showed a positive result by the thin film device of the present invention. This is consistent with the results of previous studies demonstrating that saliva samples are more useful for VZV detection.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is indicated by the following claims, and all changes or modifications derived from the meaning and scope of the claims and equivalent concepts should be interpreted to be included in the scope of the present invention.

---

The invention claimed is:

1. A method of capturing a pathogen comprising:
a first step of modifying an object by introducing an amine group to prepare a modified object; and
a second step of contacting a sample containing a pathogen on the modified object with a compound represented by Chemical Formula 1 to capture the pathogen,

[Chemical Formula 1]

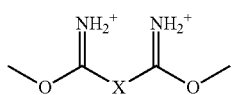

wherein X is $(CH_2)_n$ and n is an integer from 5 to 6.

2. The method of capturing a pathogen of claim 1, wherein the object of the first step is a thin film device, a magnetic bead, a ring resonator or a nanoparticle.

3. The method of capturing a pathogen of claim 1, wherein the object of the first step is modified with a silane compound.

4. The method of capturing a pathogen of claim 3, wherein the silane compound is a compound represented by Chemical Formula 2:

[Chemical Formula 2]

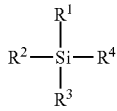

wherein each of $R^1$ to $R^3$ may be same or different, and are any one of C1 to C4 alkyl or C1 to C4 alkoxy, and $R^4$ is any one of amino (C1 to C10) alkyl, 3-(2-amino (C1 to C4)alkylamino) (C1 to C4)alkyl or 34242-amino (C1 to C4)alkylamino) (C1 to C4) alkylamino] (C1 to C4)alkyl.

5. The method of capturing a pathogen of claim 4, wherein the silane compound is at least one selected from the group consisting of (3-aminopropyl) triethoxysilane (APTES), (3-aminopropyl)trimethoxysilane), (1-aminomethyl)triethoxysilane, (2-aminoethyl)triethoxysilane, (4-aminobutyl)triethoxysilane), (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl]diethylenetriamine, [3-(2-aminoethylamino)propyl] trimethoxysilane (AEAPTMS) and 3-[(trimethoxysilyl)propyl]diethylenetriamine (TMPTA).

6. The method of capturing a pathogen of claim 1, wherein the sample containing a pathogen is any one selected from the group consisting of feces, urine, tears, saliva, external secretions from skin, external secretions from respiratory tract, external secretions from intestinal tract, external secretions from digestive tract, plasma, serum, blood, spinal fluid, lymph fluid, body fluids and tissues of object suspected of being infected with the pathogen.

7. A method of capturing a pathogen and extracting nucleic acids from the captured pathogen simultaneously, comprising:
a first step of modifying an object by introducing an amine group to prepare a modified object;
a second step of contacting a sample containing a pathogen on the modified object with a compound represented by Chemical Formula 1 to capture the pathogen;
a third step of separating nucleic acids from the captured pathogen;
a fourth step of forming a complex of the separated nucleic acids and the compound; and
a fifth step of extracting the nucleic acids by treating an elution buffer with the object in which the complex is formed,

[Chemical Formula 1]

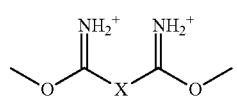

wherein X is $(CH_2)_n$ and n is an integer from 5 to 6.

8. The method of capturing a pathogen and extracting nucleic acids from the captured pathogen simultaneously of claim 7, wherein the pathogen is microorganism.

9. The method of capturing a pathogen and extracting nucleic acids from the captured pathogen simultaneously of claim 8, wherein the microorganism is virus, bacteria, fungi, protozoa, *Rickettsia* or *spirochaeta*.

10. The method of capturing a pathogen and extracting nucleic acids from the captured pathogen simultaneously of claim 7, wherein the object of the first step is a thin film device, a magnetic bead, a ring resonator or a nanoparticle.

11. The method of capturing a pathogen and extracting nucleic acids from the captured pathogen simultaneously of claim 7, wherein the object of the first step is modified with a silane compound.

12. The method of capturing a pathogen and extracting nucleic acids from the captured pathogen simultaneously of claim 11, wherein the silane compound is a compound represented by Chemical Formula 2:

[Chemical Formula 2]

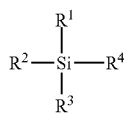

wherein each of $R^1$ to $R^3$ may be same or different, and are any one of C1 to C4 alkyl or C1 to C4 alkoxy, and $R^4$ is any one of amino (C1 to C10) alkyl, 3-(2-amino (C1 to C4)alkylamino) (C1 to C4)alkyl or 3-[2-(2-amino (C1 to C4)alkylamino) (C1 to C4) alkylamino] (C1 to C4)alkyl.

13. The method of enriching capturing a pathogen and extracting nucleic acids from the captured pathogen simultaneously of claim 12, wherein the silane compound is at least one selected from the group consisting of (3-aminopropyl) triethoxysilane (APTES), (3-aminopropyl) trimethoxysilane), (1-aminomethyl)triethoxysilane, (2-aminoethyl)triethoxysilane, (4-aminobutyl)triethoxysilane), (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl]diethylenetriamine, [3-(2-aminoethylamino)propyl]trimethoxysilane (AEAPTMS) and 3-[(trimethoxysilyl)propyl]diethylenetriamine (TMPTA).

14. The method of capturing a pathogen and extracting nucleic acids from the captured pathogen simultaneously of claim 7, wherein the sample containing a pathogen is any one selected from the group consisting of feces, urine, tears, saliva, external secretions from skin, external secretions from respiratory tract, external secretions from intestinal tract, external secretions from digestive tract, plasma, serum, blood, spinal fluid, lymph fluid, body fluids and tissues of object suspected of being infected with the pathogen.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Primer (rodA foward)

<400> SEQUENCE: 1
gcaaaccacc tttggtcg                                                 18

<210> SEQ ID NO 2
<211> LENGTH: 20
<212> TYPE: DNA
<213> ORGANISM: Artificial Sequence
<220> FEATURE:
<223> OTHER INFORMATION: Primer (rodA reverse)

<400> SEQUENCE: 2
ctgtgggtgt ggattgacat                                               20

<210> SEQ ID NO 3
<211> LENGTH: 20
<212> TYPE: DNA
<213> ORGANISM: Artificial Sequence
<220> FEATURE:
<223> OTHER INFORMATION: Primer (S segment foward)

<400> SEQUENCE: 3
cagccacttt acccgaacat                                               20
```

```
<210> SEQ ID NO 4
<211> LENGTH: 20
<212> TYPE: DNA
<213> ORGANISM: Artificial Sequence
<220> FEATURE:
<223> OTHER INFORMATION: Primer (S segment reverse)

<400> SEQUENCE: 4
ggcctactct ctgtggcaag                                              20
```